(12) United States Patent
Bartels et al.

(10) Patent No.: US 9,346,763 B2
(45) Date of Patent: May 24, 2016

(54) PROCESS FOR THE PREPARATION OF PYRAZOLE CARBOXYLIC ACID DERIVATIVES

(71) Applicant: Hoffmann-La Roche Inc., Little Falls, NJ (US)

(72) Inventors: Bjoern Bartels, Schopfheim (DE); Fritz Bliss, Hartheim (DE); Katrin Groebke Zbinden, Liestal (CH); Matthias Koerner, Grenzach-Wyhlen (DE)

(73) Assignee: Hoffman-La Roche Inc., Little Falls, NJ (US)

( * ) Notice: Subject to any disclaimer, the term of this patent is extended or adjusted under 35 U.S.C. 154(b) by 0 days.

(21) Appl. No.: 14/623,372

(22) Filed: Feb. 16, 2015

(65) Prior Publication Data

US 2015/0158818 A1 Jun. 11, 2015

Related U.S. Application Data

(63) Continuation of application No. PCT/EP2013/066953, filed on Aug. 14, 2013.

(30) Foreign Application Priority Data

Aug. 17, 2012 (EP) ..................................... 12180802

(51) Int. Cl.
| | | |
|---|---|---|
| *C07D 231/14* | (2006.01) | |
| *C07C 281/04* | (2006.01) | |
| *C07C 227/16* | (2006.01) | |
| *C07C 269/04* | (2006.01) | |
| *C07C 281/02* | (2006.01) | |

(52) U.S. Cl.
CPC ............ *C07D 231/14* (2013.01); *C07C 227/16* (2013.01); *C07C 269/04* (2013.01); *C07C 281/02* (2013.01); *C07C 281/04* (2013.01)

(58) Field of Classification Search
None
See application file for complete search history.

(56) References Cited

FOREIGN PATENT DOCUMENTS

WO 2011/117264 A1 9/2011

OTHER PUBLICATIONS

Hanzlowsky et al., "Regioselective Synthesis of Ethyl Pyrazolecarboxylates from Ethyl 3-[(Dimethylamino)methylidene]pyruvate and Diethyl 3-[(Dimethylamino)methylidene]-2-oxosuccinate. Isolation of Ethyl 4,5-Dihydro-1-heteroaryl-5-hydroxy-1H-pyrazole-5-carboxylates as Stable Intermediates in the Pyrazole Ring Formation" Journal of Heterocyclic Chem 40(3):487-498 ( 2003).
ISR for PCT/EP2013/066953.
Written Opinion of International Searching Authority for International Application No. PCT/EP2013/066953 Received on Nov. 8, 2013 4 Pages.

*Primary Examiner* — Samantha Shterengarts

(57) ABSTRACT

The present invention relates to a novel process for the preparation of a pyrazole carboxylic acid derivative of the formula

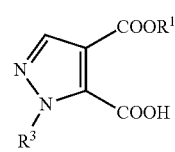

wherein $R^1$ is $C_{1-7}$-alkyl and $R^3$ is $C_{1-7}$-alkyl which is optionally substituted with halogen or $C_{1-4}$-alkoxy. The pyrazole carboxylic acid derivative of the formula I can be used as building block in the preparation of pharmaceutically active principles e.g. for compounds acting as phosphodiesterase (PDE) inhibitors, particularly PDE10 inhibitors. PDE10 inhibitors have the potential to treat psychotic disorders like schizophrenia.

16 Claims, No Drawings

PROCESS FOR THE PREPARATION OF PYRAZOLE CARBOXYLIC ACID DERIVATIVES

CROSS REFERENCE TO RELATED APPLICATIONS

This application is a continuation of International Application No. PCT/EP2013/066953 filed on Aug. 14, 2013, which is entitled to the priority of EP Application 12180802.6 filed on Aug. 17, 2012, the disclosures of which are incorporated herein by reference.

BACKGROUND OF THE INVENTION

A synthetic approach to the pyrazole carboxylic acid derivative of the formula I has been described in scheme 3 of the Int. Patent Publication WO 2011/117264 applying a method disclosed in Hanzlowsky et al., *J. Heterocyclic Chem.* 2003, 40(3), 487-489.

However, under the acid-catalyzed cyclocondensation conditions described, besides of the desired isomer, also a substantial amount of the undesired N-1 substituted isomer was formed. In many cases, especially on larger scale, this undesired isomer is the major product in the reaction mixture with ratios of up to 70:30 in favor of the undesired isomer, leading to isolated yields of ca. 30% of the undesired isomer, along with ca. 25% of the desired isomer.

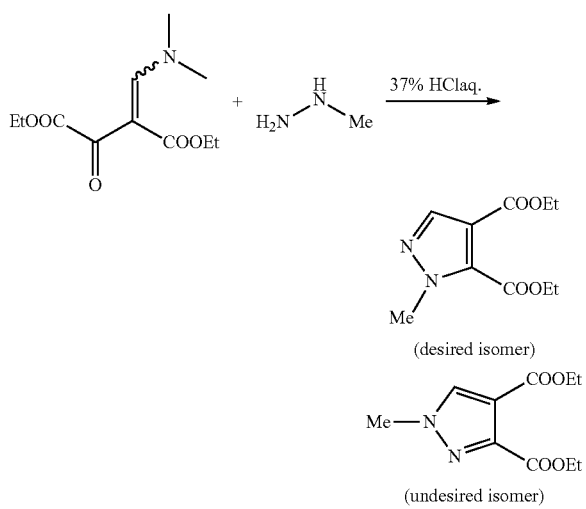

Separation of the desired from the undesired isomer, e.g. in the example described above, could only be achieved by applying chromatography techniques. Such methods are not desired for technical scale synthesis, due to economic and ecologic considerations.

SUMMARY OF THE INVENTION

The present invention relates to a novel process for the preparation of a pyrazole carboxylic acid derivative of the formula

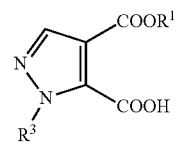

wherein $R^1$ is $C_{1-7}$-alkyl and $R^3$ is $C_{1-7}$-alkyl which is optionally substituted with halogen or $C_{1-4}$-alkoxy.

The pyrazole carboxylic acid derivative of the formula I can be used as building block in the preparation of pharmaceutically active principles, e.g. for compounds acting as phosphodiesterase (PDE) inhibitors, particularly PDE10 inhibitors. PDE10 inhibitors have the potential to treat psychotic disorders like schizophrenia (Int. Patent Publication WO 2011/117264).

Object of the present invention therefore was to find a synthetic approach which allows a more selective and a more scalable access to the desired pyrazole carboxylic acid derivative of the formula I.

The object could be achieved with the process of the present invention, as described below.

This process for the preparation of a pyrazole carboxylic acid derivative of the formula

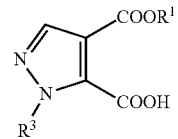

wherein $R^1$ is $C_{1-7}$-alkyl and $R^3$ is $C_{1-7}$-alkyl which is optionally substituted with halogen or $C_{1-4}$-alkoxy comprises the steps, a) reacting an oxoacetate of the formula $$R^2O \underset{O}{\overset{O}{\vphantom{X}}} X$$

II wherein $R^2$ is $C_{1-7}$-alkyl and X is halogen with an acrylate of the formula $$R^4 \underset{R^5}{N} \diagup\kern-0.5em\diagdown \underset{O}{\overset{O}{\vphantom{X}}} OR^1$$

III wherein $R^1$ is as above and $R^4$ and $R^5$ are $C_{1-7}$-alkyl in the presence of a base to form an aminomethylene succinic ester of the formula

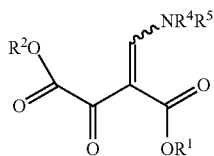

wherein $R^1$, $R^2$, $R^4$ and $R^5$ are as above;

b) coupling the aminomethylene succinic ester of the formula IV with an N-protected hydrazine derivative of formula

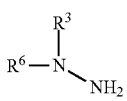

wherein $R^3$ is as above and $R^6$ is an amino protecting group to form the hydrazinomethylene succinic acid ester of the formula

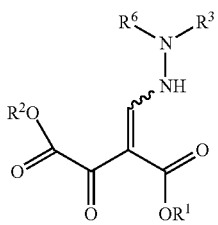

wherein $R^1$, $R^2$, $R^3$ and $R^6$ are as above;

c) ring closing the hydrazinomethylene succinic acid ester of formula VI under acidic conditions to form the pyrazole dicarboxylic acid ester of the formula

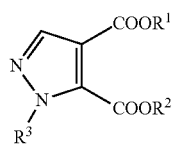

wherein $R^1$, $R^2$ and $R^3$ are as above and;

d) hydrolyzing the pyrazole dicarboxylic acid ester of the formula VII in 3-position with a base to form the pyrazole carboxylic acid derivative of the formula I.

DETAILED DESCRIPTION OF THE INVENTION

Unless otherwise indicated the following definitions are set forth to illustrate and define the meaning and scope of the various terms used to describe the invention herein.

The term $C_{1-7}$-alkyl alone or combined with other groups, refers to a branched or straight chained monovalent saturated aliphatic hydrocarbon radical of one to seven carbon atoms. This term can be exemplified by radicals like methyl, ethyl, n-propyl, i-propyl, n-butyl, s-butyl, t-butyl, pentyl, hexyl and heptyl and its isomers.

Likewise the term $C_{1-4}$-alkyl alone or combined with other groups, refers to a branched or straight chained monovalent saturated aliphatic hydrocarbon radical of one to four carbon atoms. This term can be exemplified by radicals like methyl, ethyl, n-propyl, i-propyl, n-butyl, s-butyl or t-butyl.

The term $C_{1-4}$-alkoxy stands for a $C_{1-4}$-alkyl group as defined above which is attached to an oxygen radical. This term can be exemplified by radicals like methoxy, ethoxy, n-propoxy, i-propoxy, n-butoxy, i-butoxy or t-butoxy.

The term "amino protecting group" refers to an acid or Lewis acid sensitive substituent conventionally used to hinder the reactivity of the amino group. Suitable acid or Lewis acid sensitive amino protecting groups are described in Green T., "Protective Groups in Organic Synthesis", 4th Ed. by Wiley Interscience, 2007, Chapter 7, 696 ff. Suitable amino protecting groups for $R^6$ can therefore be selected from Boc (t-butoxycarbonyl), Fmoc (fluorenylmethoxycarbonyl), Cbz (benzyloxycarbonyl), Moz (p-methoxybenzyl carbonyl), Troc (2,2,2-trichloroethoxycarbonyl), Teoc (2-(Trimethylsilyl)ethoxycarbonyl), Adoc (adamantoxycarbonyl), formyl, acetyl or cyclobutoxycarbonyl. More particularly Boc is used.

The term halogen refers to fluorine, chlorine, bromine or iodine, particularly to fluorine, chlorine or bromine.

In the graphical representations of compounds of formulae IV and VI, a wavy line indicates the existence of two possible isomers, E- and Z-, across the attached double bond. In this case, the representation refers to both, E- or Z-isomers, as single isomers or as mixtures thereof.

Step a:

Step a) requires the reaction of the oxoacetate of the formula II with an acrylate of the formula III to form an aminomethylene succinic acid ester of the formula IV.

Both the oxoacetates of formula II and the acrylates of formula III are starting compounds which are either commercially available or can be synthesized by methods known in the art.

The ethyl-2-chloro-2-oxoacetate (X=Cl and $R^2$=ethyl) and the ethyl 3-(dimethylamino)acrylate ($R^4$, $R^5$=methyl and $R^1$=ethyl) are particularly useful as starting materials.

The reaction is performed in the presence of a base which can be selected from a $C_{1-4}$-trialkylamine ideally combined with a catalytic amount of 4-(dimethylamino)-pyridine or from pyridine. Particular useful $C_{1-4}$-trialkylamines are trimethylamine, diisopropylethylamine or triethylamine.

As a rule the reaction takes place in an aprotic organic solvent, such as in 2-methyltetrahydrofuran, dichloromethane, toluene, tert-butylmethylether or tetrahydrofuran or in mixtures thereof at reaction temperatures between −20° C. and 40° C., particularly between −5° C. and 30° C.

The aminomethylene succinic acid ester of the formula IV can be isolated from the reaction mixture using methods known to the skilled in the art, however in a particular embodiment of the invention, the succinic acid ester of the formula IV is not isolated i.e. synthesis steps a) and b) are combined.

Step b):

Step b) requires the coupling of the aminomethylene succinic acid ester of the formula IV with an N-protected hydrazine derivative of formula V to form the hydrazinomethylene succinic acid ester of the formula VI.

The N-protected hydrazine derivative of formula V is either commercially available or can be synthezised by methods known in the art, e.g. as described in Int. Patent Publ. WO 2011/140425 or by Park et al. in European Journal of Organic Chemistry 2010, pages 3815-3822, or by analogous methods known to the person skilled in the art.

As outlined above once the reaction in step a) is completed step b) can be added without the isolation of the reaction product of step a).

Following the definition of the amino protecting group $R^6$ as outlined above suitable protected hydrazine derivatives of formula V can be selected from but are not limited to N-Boc-N-methylhydrazine, N-Boc-N-ethylhydrazine, N-Boc-N-n-propylhydrazine, N-Cbz-N-methylhydrazine, N-Fmoc-N-methylhydrazine, N-Moz-N-methylhydrazine, N-Troc-N-methylhydrazine, N-Teoc-N-methylhydrazine, N-Adoc-N-methylhydrazine. N-formyl-N-methylhydrazine. N-acetyl-N-methylhydrazine. N-cyclobutoxycarbonyl-N-methylhydrazine.

Particularly N-Boc-N-methylhydrazine is used.

The reaction can be performed in a polar aprotic or protic organic solvent, such as in 2-methyltetrahydrofuran, ethanol, methanol, ethyl acetate, isopropyl acetate, tetrahydrofuran, tert-butylmethylether, acetic acid, or mixtures thereof at reaction temperatures between −10° C. and 60° C., particularly between 0° C. and 40° C.

If steps a) and b) are combined the reaction can be performed in a polar aprotic organic solvent, such as in 2-methyltetrahydrofuran, tetrahydrofuran, tert-butylmethylether, or mixtures thereof at reaction temperatures between −10° C. and 60° C., particularly between 0° C. and 40° C.

Advantageously, a catalytic or stoichiometric amount of an acid which is not able to affect the amino protecting group such as phosphoric acid or acetic acid can be added.

The reaction mixture can be concentrated in vacuo at temperatures between 10° C. and 50° C., particularly between 15° and 35° C. to drive the reaction to completion.

The resulting hydrazinomethylene succinic acid ester of the formula VI can be obtained in crystalline form after concentration of the reaction mixture.

Further purification can be reached by dissolving the crystalline residue in a lower aliphatic alcohol such as in methanol and by adding water to invoke crystallization, or by recrystallization from an organic solvent, such as tert-butylmethyl-ether.

The hydrazinomethylene succinic acid esters of the formula

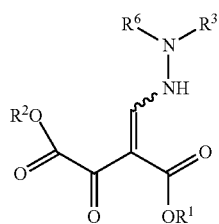

VI wherein W and $R^2$ are $C_{1-7}$-alkyl and $R^3$ is $C_{1-7}$-alkyl which is optionally substituted with halogen or $C_{1-4}$-alkoxy and $R^6$ stands for an amino protecting group are compounds not described in the art and thus represent a further embodiment of the present invention.

Particular hydrazinomethylene succinic acid esters of formula VI are those wherein $R^1$, $R^2$ and $R^3$ are $C_{1-4}$-alkyl and $R^6$ is an amino protecting group selected from Boc, Fmoc, Cbz, Moz, acetyl or formyl.

More particular compounds of formula VI carry the following substitution pattern:

| $R^1$ | $R^2$ | $R^3$ | $R^6$ |
|-------|-------|-------|-------|
| ethyl | ethyl | methyl | Boc |
| methyl | ethyl | methyl | Boc |
| ethyl | methyl | methyl | Boc |
| ethyl | ethyl | ethyl | Boc |
| methyl | ethyl | ethyl | Boc |
| ethyl | methyl | ethyl | Boc |
| ethyl | ethyl | n-propyl | Boc |
| methyl | ethyl | n-propyl | Boc |
| ethyl | methyl | n-propyl | Boc |

Step c)

Step c) requires ring closing of the hydrazinomethylene succinic acid ester of formula VI under acidic conditions to form the pyrazole dicarboxylic acid ester of the formula VIII.

The ring closing is usually performed with an inorganic acid, an organic acid or a Lewis acid in a polar solvent such as in ethylacetate, ethanol, methanol, water, tetrahydrofuran, dioxan, acetic acid, or mixtures thereof, at reaction temperatures between 0° C. and 60° C., more particularly between 10° C. and 50° C.

Suitable inorganic or organic acids are, for example, hydrochloric acid, hydrobromic acid, trifluoroacetic acid orp-toluenesulfonic acid. A suitable Lewis acid is, for example, trimethylsilyliodide. Usually hydrochloric acid is used which, can be generated in situ, e.g. by adding a lower aliphatic alcohol, e.g. ethanol to a solution of acetyl chloride in a suitable polar solvent, e.g. ethylacetate.

The pyrazole dicarboxylic acid ester of the formula VII can be isolated from the reaction mixture applying methods known to the skilled in the art, e.g. by adding water to the reaction mixture and by subsequent extraction of the reaction product with a suitable solvent, such as with ethylacetate.

Step d:

Step d) requires hydrolyzing the pyrazole dicarboxylic acid ester of the formula VII in 3-position with a base to form the pyrazole carboxylic acid derivative of the formula I.

The base as a rule is an aqueous solution of an alkali hydroxide selected from lithium-, sodium-, potassium-, or cesium hydroxide or of an alkali hydrogencarbonate selected from sodium- or potassium hydrogen carbonate. Lithium hydroxide is particularly used.

A polar aprotic or protic solvent like tetrahydrofuran, N-methylpyrrolidone, ethanol or methanol, or mixtures thereof may be used for dissolving the pyrazole dicarboxylic acid ester of the formula VII.

The hydrolysis can be performed at reaction temperatures between −20° C. and 80° C., particularly between −10° C. and 30° C.

After completion of the reaction the desired product can be isolated in crystalline form by applying methods known to the skilled in the art e.g. by acidifying the aqueous phase which has been previously washed with a suitable solvent such as dichloromethane.

EXAMPLES

General Part

All solvents and reagents were obtained from commercial sources and were used as received. All reactions were followed by TLC (thin layer chromatography, TLC plates F254, Merck), LC (liquid chromatography) or GC (gas chromatography) analysis. Proton nuclear magnetic resonance (1H NMR) spectra were obtained on Bruker 300, 400 or 600 MHz instruments with chemical shifts (δ in ppm) reported relative to tetramethylsilane as internal standard in the following format: chemical shift in ppm (peak form, coupling constants if applicable, integral). In case of a mixture of isomers, both peaks are reported in the format chemical shift of peak 1 & peak 2 in ppm (peak forms, coupling constants if applicable, integral, isomers). NMR abbreviations are as follows: s, singlet; d, doublet; t, triplet; q, quadruplet; quint, quintuplet; sext, sextuplet; hept, heptuplet; m, multiplet; br, broadened. Purity was analyzed by reverse phase HPLC or GC. Mass spectra were recorded on an Agilent 6520 QTOF spectrometer for ESI (electrospray ionization) & APCI (atmospheric pressure chemical ionization), that is achieved simultaneously (multimode), and on an Agilent 5975 instrument for EI (electron ionization) mode, with either positive (standard case, not especially noted) or negative (neg.) charged ion detection. Further used abbreviations are: IPC, internal process control; DMAP, 4-(dimethylamino)pyridine.

Example 1

2-[1-Dimethylamino-methylidene]-3-oxo-succinic acid diethyl ester

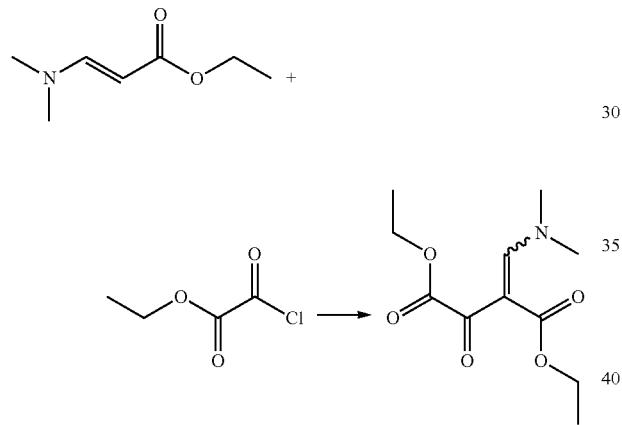

Ethyl 2-chloro-2-oxoacetate (99 g, 725 mmol) was dissolved in 2-methyltetrahydrofuran (800 ml) and 4-(dimethylamino)-pyridine (1.25 g, 10.0 mmol) was added. The mixture was cooled to −5° C. and a solution of triethylamine (76.2 g, 753 mmol) and (E)-ethyl 3-(dimethylamino)acrylate (106 g, 740 mmol) in 2-methyltetrahydrofuran (70 ml) was added via dropping funnel. The mixture was stirred for 3 h at ca. 0° C. After that, 5% (m/m) aqueous sodium chloride solution (250 mL) was added, the mixture was concentrated in vacuo to remove the 2-methyltetrahydrofuran. Ethyl acetate (800 mL) and 5% (m/m) aqueous sodium chloride solution (250 mL) were added, the organic phase was washed with 5% (m/m) aqueous sodium chloride solution (4×250 mL), the combined aqueous layers reextracted with ethyl acetate (2×300 mL) and the combined organic extracts concentrated in vacuo. The residue was filtered over silica gel (500 g, eluting with ethyl acetate/n-heptane 3:2 (v/v)) and the combined filtrates concentrated in vacuo to afford 146 g crude product as an orange oil. The crude product was dissolved at room temperature in tert-butylmethylether (1 L) and cooled to 1° C. Crystallization started at ca. 13° C. The suspension was filtered and washed with few cold tert-butylmethylether to afford 116.6 g of the title compound as light yellow crystals (66%, purity 99.9% by HPLC). MS (GC-split): m/z=243 [M]+. 1H NMR (CDCl3, 600 MHz); δ 1.26 (t, J=7.1 Hz, 3H), 1.36 (t, J=7.1 Hz, 3H), 3.03 (s, 3H), 3.36 (s, 3H), 4.17 (q, J=7.1 Hz, 2H), 4.30 (q, J=7.1 Hz, 2H), 7.85 (s, 1H). The product was isolated as single isomer.

Example 2

2-(N'-tert-Butoxycarbonyl-N'-methylhydrazinomethylene)-3-oxo-succinic acid di-ethyl ester

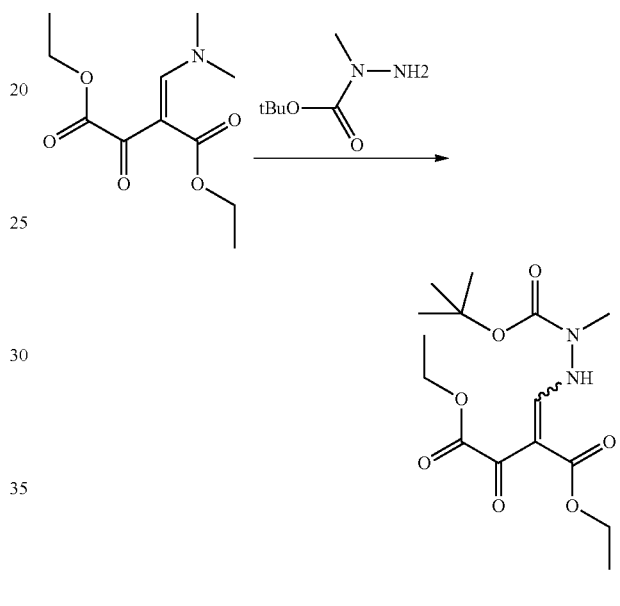

In a 1500 mL jacket controlled reaction flask equipped with mechanical stirrer, condenser and internal thermometer 2-[1-dimethylamino-meth-(Z)-ylidene]-3-oxo-succinic acid diethyl ester (73.2 g, 301 mmol) was dissolved in ethyl acetate (700 ml) and the solution was cooled to −5° C. A solution of N-tert-butoxycarbonyl-N-methylhydrazine (61.5 g, 421 mmol) in ethyl acetate (60 mL) was added dropwise within 45 min. The reaction mixture was stirred for 30 min at −5° C. Then, it was concentrated in vacuo to a volume of 100 mL and at a constant volume, solvent was exchanged with tert-butylmethylether (1.6 L), resulting in a thick suspension. More tert-butylmethylether (400 mL) was added, the suspension was stirred for 1 h at 0° C., filtered and the precipitate was washed with cold tert-butylmethylether (200 mL). After drying in vacuo (45° C., 20 mbar) the title compound was obtained as a colorless crystalline solid (93.2 g, 90%). MS (ESI & APCI, neg.): m/z=343.15 [M−H]−. 1H NMR (CDCl3, 600 MHz); δ 1.29 (t, J=7.1 Hz, 3H), 1.37 & 1.37 (2t, J=7.1 Hz, 3H, isomers), 1.48 & 1.48 (2s, 9H, isomers), 3.23 & 3.24 (2s, 3H, isomers), 4.22 & 4.24 (2q, J=7.1 Hz, 2H, isomers), 4.31 & 4.35 (2q, J=7.1 Hz, 2H, isomers), 8.07 & 8.12 (2d, J=10.3 Hz & 11.6 Hz, 1H, isomers), 11.51 & 11.53 (2br, 1H, isomers). The isolated product is a mixture of (E)- and (Z)-isomers.

Example 3

2-(N'-tert-Butoxycarbonyl-N'-methylhydrazinomethylene)-3-oxo-succinic acid diethyl ester (telescoped process)

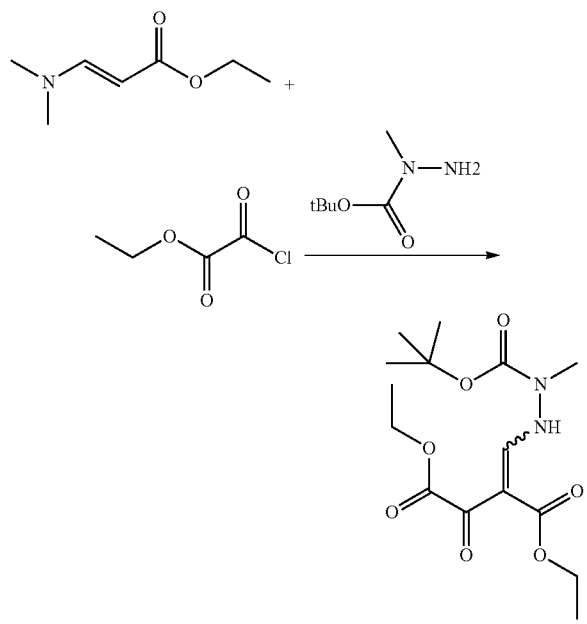

Process Variant 1:

In a 12 L jacket controlled vessel equipped with mechanical stirrer, condenser, internal thermometer and inert gas supply, ethyl 2-chloro-2-oxoacetate (192 g, 158 mL, 1.38 mol) was dissolved under argon at 20° C. in 2-methyltetrahydrofuran (1.34 L). DMAP (2.41 g, 19.3 mmol) was added as solid to the clear, colorless solution. The mixture was cooled to 2° C. internal temperature. A solution of (E)-ethyl 3-(dimethylamino)acrylate (179 g, 1.24 mol) in 2-methyltetrahydrofuran (960 mL) and triethylamine (154 g, 212 mL, 1.51 mol) was prepared in a separate flask by subsequent addition at room temperature, and added to the solution of ethyl 2-chloro-2-oxoacetate and DMAP at a rate that the internal temperature was kept at ca. 2° C. (cooling necessary). The mixture became cloudy, later a thick crystal mash (still stirrable). After 30 min stirring at 2° C., the mixture was warmed to room temperature, filtered, the precipitate was washed with 2-methyltetrahydrofuran (2 L). N-tert-Butoxycarbonyl-N-methylhydrazine (250 g, 254 mL, 1.66 mol) was added to the combined filtrate at 20° C. and the resulting mixture was stirred for 1 h. After that, the reaction mixture was concentrated in vacuo to an orange crystalline residue. The residue was dissolved in methanol (4 L, dark red solution) and water (4 L) was added. The product crystallized spontaneously, the slurry was stirred over night at room temperature. The mixture was filtered, the crystalline precipitate subsequently washed with water (8 L) and heptane (8 L), and dried over night at 50° C. and 12 mbar to afford 352 g of desired product as white powder (83%). M.p. 130.2-131.3° C. MS (ESI & APCI, neg.): m/z=343.15 [M−H]−. 1H NMR (CDCl$_3$, 600 MHz); δ 1.29 (t, J=7.1 Hz, 3H), 1.37 & 1.37 (2t, J=7.1 Hz, 3H, isomers), 1.48 & 1.48 (2s, 9H, isomers), 3.23 & 3.24 (2s, 3H, isomers), 4.22 & 4.24 (2q, J=7.1 Hz, 2H, isomers), 4.31 & 4.35 (2q, J=7.1 Hz, 2H, isomers), 8.07 & 8.12 (2d, J=10.3 Hz & 11.6 Hz, 1H, isomers), 11.51 & 11.53 (2br s, 1H, isomers). The isolated product is a mixture of (E)- and (Z)-isomers.

Process Variant 2:

A 300 L reactor equipped with temperature control and vacuum system was charged under nitrogen atmosphere with (E)-ethyl 3-(dimethylamino)acrylate (10.0 kg, 69.8 mol), tetrahydrofuran (80 kg), triethylamine (8.6 kg, 85.0 mol) and DMAP (0.14 kg, 1.25 mol) and the resulting solution was cooled to −5-0° C. A solution of ethyl 2-chloro-2-oxoacetate (11.0 kg, 80.6 mol) in tetrahydrofuran (9 kg) was added dropwise to the mixture at a rate that the internal temperature was kept at −5-0° C. (within ca. 3 h). Then, the mixture was warmed to 15-25° C. and stirred for 40 min or until IPC showed complete consumption of (E)-ethyl 3-(dimethylamino)acrylate. N-tert-Butoxycarbonyl-N-methylhydrazine (13.5 kg, 85.7 mol) was added to the mixture within ca. 5 min. The solvent was removed by evaporation and the mixture was heated to ca. 30-35° C. The evaporation was stopped when tetrahydrofuran distillation ceased (after ca. 4 h). The obtained semi-solid was cooled to 20-25° C. Methanol (39.6 kg) was added and the mixture was stirred for 10 min. Water (110 kg) was added at internal temperature 15-20° C. within 10 min. The mixture was stirred for 2 h at 15-25° C., filtered and the filtered precipitate washed subsequently with water (2×25 kg) and n-heptane (2×16.7 kg). It was then dried at 50-55° C. for 10 h to obtain the title compound as a white solid (21.0 kg, 85.0%, purity 99.2% by HPLC). The isolated product is a mixture of (E)- and (Z)-isomers, product identity was confirmed by 1H NMR and MS.

Example 4

2-Methyl-2H-pyrazole-3,4-dicarboxylic acid diethyl ester

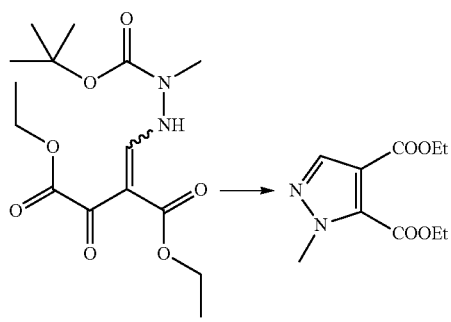 [SMILES: CCOC(=O)C(=O)C(=CNN(C)C(=O)OC(C)(C)C)C(=O)OCC ; CCOC(=O)c1cnn(C)c1C(=O)OCC]

Process Variant 1:

A 12 L jacket controlled vessel equipped with mechanical stirrer, condenser, internal thermometer and inert gas supply was charged with ethyl acetate (2.21 kg, 2.45 L, 25.0 mol) under argon at 20° C. Acetyl chloride (564 g, 511 mL, 7.11 mol) was added (slight exotherm, clear colorless solution). Ethanol (656 g, 826 mL, 14.2 mol) was added at a rate that the internal temperature was kept at 20-25° C. (process-controlled, strongly exothermic, efficient cooling necessary). A suspension of (Z)-diethyl 2-((2-(tert-butoxycarbonyl)-2-methylhydrazinyl)methylene)-3-oxosuccinate (350 g, 1.02 mol) in ethyl acetate (1.05 L) was added via pump at 20° C. to the anhydrous hydrochloric acid solution in ethyl acetate/ethanol. The resulting white suspension became a greenish solution, no exothermy. The mixture was stirred at 50° C. for 2 h. After that, the mixture was cooled to 20° C. and water (6 L) was added (slight exotherm, internal temp. 34° C., rapid phase separation). After phase separation, the aqueous phase was extracted with ethyl acetate (2×1 L). The combined organic extracts were dried (sodium sulfate) and concentrated in vacuo (50° C. jacket temperature, 10 mbar) to obtain 236 g crude product as a yellow oil (99%, purity 96.8% by HPLC). MS (ESI & APCI): m/z=227.1 [M+H]+. 1H NMR (CDCl3, 600 MHz); δ 1.34 (t, J=7.1 Hz, 3H), 1.41 (t, J=7.1 Hz, 3H), 4.02 (s, 3H), 4.30 (q, J=7.1 Hz, 2H), 4.44 (q, J=7.1 Hz, 2H), 7.82 (s, 1H).

Process Variant 2:

A 300 L reactor equipped with temperature control and vacuum system was charged with a solution of hydrogen chloride in ethanol (58.6 kg, assay: 38.6% m/m, 620 mol) and the solution was cooled to ca. 0-5° C. (Z)-Diethyl 2-((2-(tert-butoxycarbonyl)-2-methylhydrazinyl)methylene)-3-oxosuccinate (58.6 kg, 171 mol) was added to the solution in portions within 50 min at 0-15° C. The mixture was then warmed to 15-25° C. and stirred for 3 h, or until IPC showed complete consumption of starting material, tert-Butylmethylether (87.9 kg) was added to the mixture and the mixture was transferred to a 500 L reactor. Water (175.8 kg) was added to the solution at a rate that the internal temperature was kept below 25° C. After phase separation, the aqueous layer was transferred to a 1000 L reactor and it was extracted with tert-butylmethylether (2×87.9 kg). The organic layer was combined in a 500 L reactor and washed subsequently with water (87.9 kg) and a solution of sodium hydrogencarbonate (4.7 kg) in water (87.9 kg), and dried over sodium sulfate (39.3 kg). The mixture was filtered and the filtrate was evaporated in vacuo at 30-55° C. to afford the title compound as a yellow liquid (36.7 kg, 95.3%, purity 99.6% by HPLC). Product identity was confirmed by 1H NMR and MS.

Example 5

2-Methyl-2H-pyrazole-3,4-dicarboxylic acid 4-ethyl ester

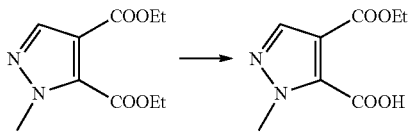 [SMILES: CCOC(=O)c1cnn(C)c1C(=O)OCC ; CCOC(=O)c1cnn(C)c1C(=O)O]

Process Variant 1:

In a 63 L steel/enamel vessel equipped with a reflux condenser combined with a thermometer, a mechanical stirrer and an inert gas supply 2-methyl-2H-pyrazole-3,4-dicarboxylic acid diethyl ester (2.84 kg, 12.6 mol) was dissolved in a mixture of tetrahydrofuran (20.0 L) and ethanol (8.5 L) under nitrogen at room temperature. The mixture was cooled to −5° C. and a solution of lithium hydroxide monohydrate (0.53 kg, 12.6 mol) in water (10.0 L) was added within 90 min at −5° C. The dropping funnel was rinsed with water (1.4 L). The reaction mixture was stirred for 95 min at −4° C. to −6° C. After that, the mixture was diluted with dichloromethane (10.0 L) and water (10.0 L) at −5° C. to 0° C. and stirred for 10 min. The organic layer was separated. The aqueous phase was washed with dichloromethane (2×10.0 L). The aqueous phase was acidified to pH<2 by addition of hydrochloric acid (2.75 kg, assay: 25% m/m, 18.8 mol) in water (2.0 L) within 15 min at 20° C. to 25° C. The resulting crystal suspension was stirred for 17 h at 22° C. Then, the crystal suspension was filtered over a glass filter funnel. The filter cake was washed successively with water (7.0 L) and n-heptane (4.0 L). The white crystals were dried in vacuo at 50° C./<5 mbar for 70 h to afford 1.99 kg of the title compound as white crystals (80%). MS (ESI & APCI): m/z=199.1 [M+H]+. 1H NMR (D6-DMSO, 600 MHz); δ 1.25 (t, J=7.1 Hz, 3H), 3.94 (s, 3H), 4.22 (q, J=7.1 Hz, 2H), 7.85 (s, 1H), 14.18 (br s, 1H).

Process Variant 2:

A 1000 L reactor equipped with temperature control and vacuum system was charged with 2-methyl-2H-pyrazole-3,4-dicarboxylic acid diethyl ester (36.5 kg, 161 mol), tetrahydrofuran (253 kg) and ethanol (20.0 L) under nitrogen at room temperature. The mixture was cooled to −10--5° C. In another 300 L reactor, a solution of lithium hydroxide monohydrate (6.47 kg, 154 mol) in water (135.8 kg) was precooled to 5-10° C. and added dropwise to the 1000 L reactor at a rate that the internal temperature was kept at −10--5° C. (ca. 3 h). The mixture was stirred at −10--5° C. for 3 h or until IPC met the specification (i.e. 2-methyl-2H-pyrazole-3,4-dicarboxylic acid diethyl ester<10% by HPLC and byproduct 2-methyl-2H-pyrazole-3,4-dicarboxylic acid<4% by HPLC). Dichloromethane (190.8 kg) and water (146.8 kg) were then added and the mixture was stirred for 20 min. The organic layer was separated, the aqueous phase was washed with dichloromethane (2×190.8 kg), after that the aqueous layer was filtered through an 8 cm plug of Celite and the filtrate was transferred to a 500 L reactor. It was cooled to 5-10° C., hydrochloric acid (18% m/m) was added dropwise within 50 min at 5-15° C. until pH=1-2 (ca. 30 kg). The product crystallized gradually as a white solid. The suspension was stirred at 25-30° C. for 10 h. The precipitate was centrifuged, washed with water (69.4 kg) and n-heptane (2×29 kg) and dried in vacuo at 40-55° C. for 48 h to afford the title compound as white solid (22.2 kg, 69.4%, purity 99.7% by GC). Product identity was confirmed by 1H NMR and MS.

The invention claimed is:

1. Process for the preparation of a pyrazole carboxylic acid derivative of the formula

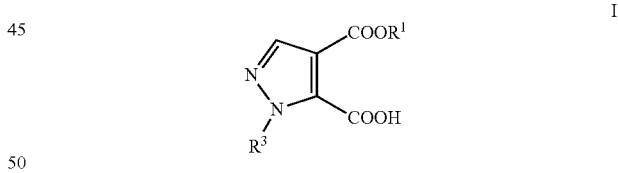

wherein $R^1$ is $C_{1-7}$-alkyl and $R^3$ is $C_{1-7}$-alkyl which is optionally substituted with halogen or $C_{1-4}$-alkoxy comprising the steps, a) reacting an oxoacetate of the formula

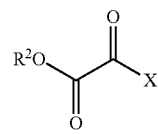

wherein $R^2$ is $C_{1-7}$-alkyl and X is halogen with an acrylate of the formula

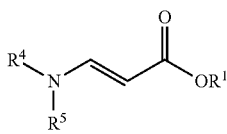

wherein $R^1$ is as above and $R^4$ and $R^5$ are $C_{1-7}$-alkyl in the presence of a base to form an aminomethylene succinic acid ester of the formula

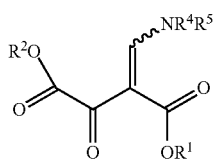

wherein $R^1$, $R^2$, $R^4$ and $R^5$ are as above;

b) coupling the aminomethylene succinic acid ester of the formula IV with an N-protected hydrazine derivative of formula

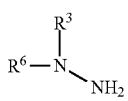

wherein $R^3$ is as above and $R^6$ is an amino protecting group to form the hydrazinomethylene succinic acid ester of the formula

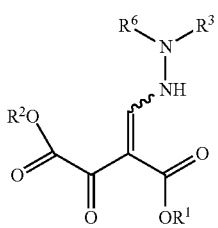

wherein $R^1$, $R^2$, $R^3$ and $R^6$ are as above;

c) ring closing the hydrazinomethylene succinic acid ester of formula VI under acidic conditions to form the pyrazole dicarboxylic acid ester of the formula

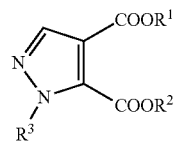

wherein $R^1$, $R^2$ and $R^3$ are as above and;

d) hydrolyzing the pyrazole dicarboxylic acid ester of the formula VII in 3-position with a base to form the pyrazole carboxylic acid derivative of the formula I.

2. Process of claim 1, wherein step a) and step b) are combined and wherein the aminomethylene succinic acid ester of the formula IV is not isolated.

3. Process of claim 1, wherein the base used in step a) can be selected from a $C_{1-4}$-trialkylamine combined with a catalytic amount of 4-(dimethylamino)-pyridine or from pyridine.

4. Process of claim 1, wherein step a) is performed in an aprotic organic solvent, or mixtures thereof, at reaction temperatures between −20° C. and 40° C.

5. Process of claim 1, wherein the N-protected hydrazine derivative of formula V used in step b) can be selected from N-Boc-N-methylhydrazine, N-Boc-N-ethylhydrazine, N-Boc-N-n-propylhydrazine, N-Cbz-N-methylhydrazine, N-Fmoc-N-methylhydrazine, N-Moz-N-methylhydrazine, N-Troc-N-methylhydrazine, N-Teoc-N-methylhydrazine, N-Adoc-N-methylhydrazine, N-formyl-N-methylhydrazine, N-acetyl-N-methylhydrazine, N-cyclobutoxycarbonyl-N-methylhydrazine.

6. Process of claim 1, wherein step b) is performed in a polar aprotic or protic organic solvent, or mixtures thereof, at reaction temperatures between −10° C. and 60° C., or, if step a) and b) are combined, wherein step b) is performed in a polar aprotic organic solvent, or mixtures thereof, at reaction temperatures between −10° C. and 60° C.

7. Process of claim 1, wherein step b) is performed in the presence of an acid, which is not able to affect the amino protecting group of the hydrazinomethylene succinic acid ester of the formula VI.

8. Process of claim 1, wherein the ring closing in step c) is performed with an inorganic acid, an organic acid or a Lewis acid in a polar solvent, or mixtures thereof, at reaction temperatures between 0° C. and 60° C.

9. Process of claim 1, wherein the base used for the ester hydrolysis in step d) is an aqueous solution of an alkali hydroxide or of an alkali hydrogencarbonate.

10. Process of claim 1, wherein the ester hydrolysis in step d) is performed at reaction temperatures between −20° C. and 80° C.

11. Process of claim 1, wherein $R^1$, $R^2$, $R^3$, $R^4$ and $R^5$ are $C_{1-4}$-alkyl.

12. Process of claim 1, wherein $R^6$ is Boc.

13. Process of claim 1, wherein X is chlorine.

14. Hydrazinomethylene succinic acid ester of the formula

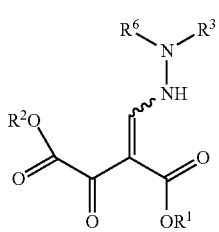

wherein $R^1$ and $R^2$ are $C_{1-7}$-alkyl and $R^3$ is $C_{1-7}$-alkyl which is optionally substituted with halogen or $C_{1-4}$-alkoxy and $R^6$ stands for an amino protecting group.

15. Hydrazinomethylene succinic acid ester of claim 14, wherein $R^1$, $R^2$ and $R^3$ are $C_{1-4}$-alkyl and $R^6$ is an amino protecting group selected from Boc, Fmoc, Cbz, Moz, acetyl or formyl.

16. Hydrazinomethylene succinic acid ester of claim 14, wherein $R^1$ and $R^2$ are methyl or ethyl, $R^3$ is methyl, ethyl or n-propyl and $R^6$ is Boc.

* * * * *